(12) United States Patent
Korten et al.

(10) Patent No.: US 11,826,215 B2
(45) Date of Patent: Nov. 28, 2023

(54) SYSTEM OF A DENTAL BLANK AND AN ASSOCIATED SHADE GUIDE

(71) Applicant: 3M INNOVATIVE PROPERTIES COMPANY, St. Paul, MN (US)

(72) Inventors: Malte Korten, Moorenweis (DE); Helmar B. Mayr, Kaufering (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 506 days.

(21) Appl. No.: 16/907,631

(22) Filed: Jun. 22, 2020

(65) Prior Publication Data
US 2020/0315761 A1    Oct. 8, 2020

Related U.S. Application Data

(62) Division of application No. 15/035,794, filed as application No. PCT/US2014/064807 on Nov. 10, 2014, now Pat. No. 10,709,534.

(30) Foreign Application Priority Data

Nov. 12, 2013    (EP) ..................... 13192571

(51) Int. Cl.
  *A61C 13/00*   (2006.01)
  *A61C 19/10*   (2006.01)
  (Continued)

(52) U.S. Cl.
  CPC .......... *A61C 19/10* (2013.01); *A61C 13/0004* (2013.01); *A61C 13/0006* (2013.01);
  (Continued)

(58) Field of Classification Search
  CPC ............ A61C 13/0004; A61C 13/0006; A61C 13/0022; A61C 13/083; A61C 19/10; A61C 13/081–09
  See application file for complete search history.

(56) References Cited

U.S. PATENT DOCUMENTS 4,657,399 A    4/1987   Hall
5,151,044 A *  9/1992   Rotsaert ............. A61C 13/0003
                                               428/542.8

(Continued)

FOREIGN PATENT DOCUMENTS

DE    19944130    4/2001
EP    2193759     6/2010
(Continued)

OTHER PUBLICATIONS

"VITA Classical Shade Guide", 2017; VITA North America, http://vitanorthamerica.com.; © 2017, 3pp.
(Continued)

*Primary Examiner* — Yogesh P Patel (57) ABSTRACT

A system having at least one dental blank and an associated shade guide. The dental blank exhibits a non-uniform color shading, and the shade guide comprises a plurality of shade specimens each exhibiting a particular color shading representing the same color shading present in a partial area within the dental blank. A method of making a dental restoration includes the use of the system. The invention facilitates making a dental restoration having a color shading resembling the color shading of a natural tooth.

10 Claims, 4 Drawing Sheets

(51) Int. Cl.
*G16H 20/40* (2018.01)
*A61C 13/08* (2006.01)
*A61C 13/083* (2006.01)
*A61C 13/09* (2006.01)

(52) U.S. Cl.
CPC ........ *A61C 13/0022* (2013.01); *A61C 13/082* (2013.01); *A61C 13/083* (2013.01); *A61C 13/09* (2013.01); *G16H 20/40* (2018.01)

(56) References Cited

U.S. PATENT DOCUMENTS

| | | | |
|---|---|---|---|
| 5,498,157 | A | 3/1996 | Hall |
| 6,379,593 | B1 | 4/2002 | Datzmann |
| 7,303,391 | B1 | 12/2007 | Alexander |
| 7,981,531 | B2 | 7/2011 | Rheinberger |
| 8,551,622 | B2 | 10/2013 | Ganley |
| 8,691,122 | B2 | 4/2014 | Rheinberger |
| 8,721,336 | B2 | 5/2014 | Rheinberger |
| 2006/0147874 | A1 | 7/2006 | Touchstone |
| 2008/0303181 | A1 | 12/2008 | Holand |
| 2011/0085713 | A1* | 4/2011 | Yan .......................... G06T 7/174 382/128 |
| 2011/0104643 | A1 | 5/2011 | Giordano |
| 2011/0125304 | A1 | 5/2011 | Schneider |
| 2012/0205828 | A1 | 8/2012 | Laubersheimer |
| 2013/0224454 | A1 | 8/2013 | Jung |
| 2013/0313738 | A1 | 11/2013 | Carden |
| 2014/0377718 | A1 | 12/2014 | Korten |
| 2016/0262860 | A1 | 9/2016 | Korten |

FOREIGN PATENT DOCUMENTS

| | | |
|---|---|---|
| WO | WO 2002-09612 | 2/2002 |
| WO | WO 2008-083358 | 7/2008 |

OTHER PUBLICATIONS

International Search Report for PCT International Application No. PCT/US2014/064807 dated Jan. 19, 2015, 3 pages.

* cited by examiner

SYSTEM OF A DENTAL BLANK AND AN ASSOCIATED SHADE GUIDE

FIELD OF THE INVENTION

The invention relates to a system having a dental blank and an associated shade guide, and in particular to a dental blank having a non-uniform color shading and a shade guide exhibiting shade specimens of the non-uniform color shading at different locations within the dental blank. The invention further relates to a method of making a dental restoration by use of the system.

BACKGROUND ART

Dental restorations are often manufactured by an automated process, which typically includes:
- capturing the shape of a patient's teeth, for example by scanning a plaster model of the patient's teeth or alternatively by scanning the actual teeth in the patient's mouth;
- designing the shape of a dental restoration precursor based on the captured shape using a computer-aided design (CAD) software; and
- machining the dental restoration precursor to correspond to the designed shape, for example, by an automated Computer Numerical Controlled (CNC) machine.

It is desirable that the dental restoration also has an appearance that matches or approximates the appearance of adjacent teeth. The appearance of natural teeth is on the one hand provided by color shades, and further by a certain translucency. A dental technician or a dental practitioner, for example, typically selects the color of the ceramic material to be used for the dental restoration according to the teeth in a patient's mouth that are located next to the tooth or teeth to be restored. For example, the appearance of relevant teeth in a patient's mouth may be determined using shade guides and the color shade for the framework and the veneer may be selected accordingly. Exemplary shade guide types are available under the designations "VITA Classical Shade Guide" or "VITA Toothguide 3D-Master®" from the company VITA Zahnfabrik H. Rauter GmbH & Co. KG, Germany. General types of materials for dental restorations are typically selected to meet certain mechanical and aesthetic requirements, which are for example the desired color and/or translucency.

Manufacturers of dental materials often offer dental restorative materials in a variety of different color shades, and a dental technician or a dental practitioner usually selects the shade of the material that is closest to the desired shade. Many approaches have been tried to provide dental restorative materials in color shades that match the desired color as closely as possible.

Although the current approaches for manufacturing of dental restorations may provide a variety of advantages, there is still a desire for a method of manufacturing dental restorations in a reproducible, cost efficient manner and at a good aesthetic quality.

SUMMARY OF THE INVENTION

The invention relates to a system which comprises at least one dental blank and an associated shade guide.

The dental blank exhibits a non-uniform color shading in at least one dimension. Further the shade guide comprises a plurality of shade specimens. Each of the shade specimens exhibits a specimen surface that has a three-dimensional shape. Further each of the shade specimens exhibits a particular color shading defined by a virtual three-dimensional target surface within the dental blank. The target surface has a shape which is equal to or which correlates to the shape of the specimen surface.

The invention is advantageous in that it allows matching a non-uniform color shading, also sometimes referred to as "color gradient", of a dental restoration and a natural tooth color shading. The term "matching" as referred to herein thereby encompasses assimilation or approximation, for example of colors. This means that for example a "matching" of colors or color shades does not require two matched colors or color shades to be exactly identical. Further the invention allows the making of a variety of different non-uniformly color shaded dental restorations from the same type of non-uniformly color shaded blanks. The invention helps maximizing flexibility for a dentist or dental technical in providing the dental restoration with a desired non-uniform color shading. Further the invention helps maximizing the reproducibility in the making of the dental restoration. For example the shade guide of the invention preferably provides unique information, for example in the form of one unique encoding, for describing a non-uniform color shade of a tooth. This is in contrast to prior approaches in which the dental practitioner had to match different colors of the same tooth with different samples of a shade guide to landmark different color codes of the shade guide on a geometric diagram of that tooth.

In one embodiment the dental blank exhibits a non-uniform color shading in two or all three dimensions. For example the non-uniform color shading may be the same in all three dimensions or different in two or three dimensions. A dental restoration obtained from such a dental blank may relatively pleasantly resemble a natural tooth.

In one embodiment the shade guide is provided in the form of a physical shade guide, having a holder allowing a user to hold the shade guide and, attached thereto, a number of physical shade specimens which exhibit the particular non-uniform color shading. Such color shading is at least provided on the on the specimen surface. The shade guide thus preferably allows presenting a plurality of different particular non-uniform color shadings to a user. As described above each particular non-uniform color shading is associated to an equivalent particular non-uniform color shading in a dental blank. Such particular non-uniform color shading is preferably defined by the virtual target surface in a particular position and orientation within the dental blank. Accordingly different particular non-uniform color shadings can be defined by different positions and/or different orientations of the target surface within the blank. This is advantageous in that one type of a non-uniform color shaded blank can be used to make a variety of differently color shaded dental restorations.

In a further embodiment the shade guide is provided in the form of a virtual shade guide, for example displayed on a computer screen. The virtual shade guide preferably has a number of virtual shade specimens which exhibit the particular non-uniform color shading. The virtual shade guide thus preferably allows presenting a plurality of different particular non-uniform color shadings to a user.

In a further embodiment the dental blank is made of differently colored materials which in combination provide the dental blank with the non-uniform color shading. Preferably the dental blank is "solid-colored". This means for example that the non-uniform color shading is provided in major volume portions of the dental blank, rather than just at an outer surface of the blank.

In one embodiment the three-dimensional shape of the specimen surface is non-planar. In particular the three-dimensional shape of the specimen surface may correspond to a standardized shape of a human incisal tooth. This facilitates a comparison of color shades between the shade specimens and a natural tooth by a user, for example a dentist, because this avoids that the same colors on differently shaped surfaces may appear different.

In a further embodiment the dental blank further exhibits a non-uniform transparency gradient in at least one dimension. Each shade specimen may represent a particular transparency gradient present in the dental blank or obtainable from the dental blank adjacent the target surface within the dental blank. The non-uniform color shading and the non-uniform transparency gradient may be combined in one blank.

Each specimen is preferably associated with a target surface of the invention. The target surface preferably has a predetermined position and orientation within the dental blank. The skilled person will recognize that the target surface is virtual and refers to a mathematical definition of a partial (virtual) cross-section having a position and orientation within the dental blank. The non-uniform color shading present at such partial cross-section is represented in one shade specimen of the shade guide. Further in a pre-sintered blank the non-uniform color shading defined by the target surface preferably refers to the same blank theoretically sintered to its final density. The target surfaces, as they are associated with different shade specimens, have at least one of different positions and different orientations in the dental blank.

In one embodiment the position of the target surface is defined by three coordinates in a three-dimensional Cartesian coordinate system. Accordingly a particular position of the target surface may be determined by an X, Y and Z coordinate. Further the orientation is preferably defined by a first inclination angle about a first axis, a second inclination angle about a second axis and a rotation angle about a third axis of the same Cartesian coordinate system. For example the first and second inclination angle may be determined by a rotation angle about the Y-axis and Z-axis, respectively, of the coordinate system, whereas the rotation angle may be determined about the Z-axis. The Cartesian coordinate system which the position and orientation are based on may have its origin at a pre-determined coordinate relative to or within the blank.

In one embodiment each specimen surface is assigned an encoding representing information about the color shading and information about the position and orientation of the target surface in the dental blank. Preferably the shade guide comprises such an encoding in the form of visible information. For example the encoding may comprise information about one or more colors present in the color shading and coordinates of the reference surface in the blank. Thus a user is enabled to read the encoding from the shade guide and for example communicate such encoding to a dental lab which manufactures the corresponding dental restoration.

In a further embodiment the dental blank is formed of a pre-sintered ceramic material having an open porous structure. In this embodiment the target surface may correspond to a proportionally enlarged shape of the specimen surface. Accordingly the position and orientation of the target surface may include an offset. This is to account for a shrinkage of the dental blank during sintering toward its final density.

In an alternative embodiment the dental blank is formed of a solid block of material (for example a glass ceramic material which is sintered to its final density or a dental composite material). In this embodiment the target surface may be equal to the shape of the specimen surface. The dental blank may be formed for example of a dental composite material, for example LAVA' Ultimate, as available from 3M Deutschland GmbH, Germany. Further the dental blank may be formed of a dental ceramic, for example zirconia or glass ceramic, for example lithium disilicate.

In a further aspect the invention relates to a method of making a dental restoration. The method comprises the steps of:
   providing a dental blank exhibiting a non-uniform color shading in at least one dimension;
   providing a shade guide that is associated to the dental blank, the shade guide comprising a plurality of shade specimens each exhibiting a specimen surface, wherein each specimen surface has a three-dimensional shape and represents a particular color shading defined by a virtual three-dimensional target surface of a correlating shape within the dental blank;
   visually matching one shade specimen of the shade guide with a tooth of a patient and thereby determine a selected shade specimen;
   using a position and/or orientation associated with the specimen and determining a correlating position and/or orientation within the dental blank; and
   machining the dental restoration, or a precursor thereof, at the correlating position and/or orientation from the dental blank.

A precursor of the dental restoration may for example be machined from a pre-sintered dental blank. Such a precursor is preferably three-dimensionally proportionally enlarged relative to the dental restoration to account for shrinking during finally sintering. A precursor of the dental restoration may further be machined from or a blank made of a dental composite material.

In one embodiment the method further comprises the steps of:
   determining the encoding associated with the selected shade specimen; and
   machining the dental restoration based on the encoding associated with the selected shade specimen.

For example the encoding may be entered by a user or dental practitioner in a machine for machining dental restorations. Such a machine may be configured to retrieve or adapt a machining program for machining the dental restoration at the appropriate position and orientation as defined via the encoding.

In one embodiment the method further comprises the steps of:
   designing the dental restoration by computer aid based on a virtual model of the dental restoration; and
   using the target surface to determine the position and/or orientation of the dental restoration, or the pre-cursor thereof, within the dental blank.

The target surface and the dental restoration model may for example be put in a determined geometric relationship relative to each other, for example on a CAD system by computer aid, so that by the position and/or orientation of the target surface relative to the blank the position and/or orientation of the dental restoration relative to the blank is also determined.

In a further embodiment the method further comprises the steps of:
   capturing a color shade of a patient's tooth by taking an image of the patient's tooth;
   displaying the color shade of the patient's tooth on a computer; and providing the shade guide virtually on the computer.

The color shade may be captured by a photo camera, for example by a photo camera of a smart phone or tablet computer, and an app on the smart phone or tablet computer may provide a virtual shade guide from which a user can select an appropriate shade specimen.

In a further embodiment the method comprises the steps of:
selecting a particular specimen for the color shade displayed on the computer;
obtaining a position and orientation of the target surface in the dental blank from the associated specimen; and
providing machine data for machining the dental restoration, or a precursor thereof, from the dental blank.

For machining the dental restoration a dental milling or grinding machine may be used.

Accordingly in a further embodiment the method comprises the steps of:
grinding the dental restoration from the dental blank; or
milling a precursor of the dental restoration from the dental blank and sintering the precursor to form the dental restoration.

DETAILED DESCRIPTION OF THE INVENTION

Figure 1:
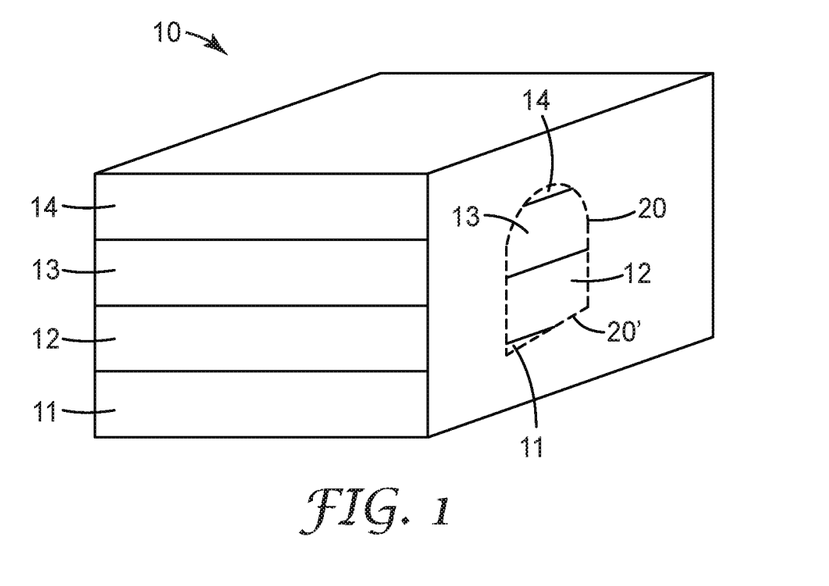
FIG. 1 is a perspective view of a dental blank according to an embodiment of the invention.

FIG. 1 shows a dental blank 10 which has a non-uniform color shading. According to the invention the dental blank may be formed of several layers each having a different color. Further the dental blank may not have discrete and distinguishable color layers, but may have a continuous non-uniform color shading, or may have similar or different color shadings in two or all three dimensions of the dental blank. For ease of explanation the illustrated example refers to a dental blank in which the non-uniform color shading extends in one dimension only (vertical in the Figure). Further in this example the blank is formed of four distinguishable differently colored layers 11, 12, 13, 14. The layers 11-14 are arranged on top of each other and thus provide the dental blank 10 with the non-uniform color shading.

Figure 2:
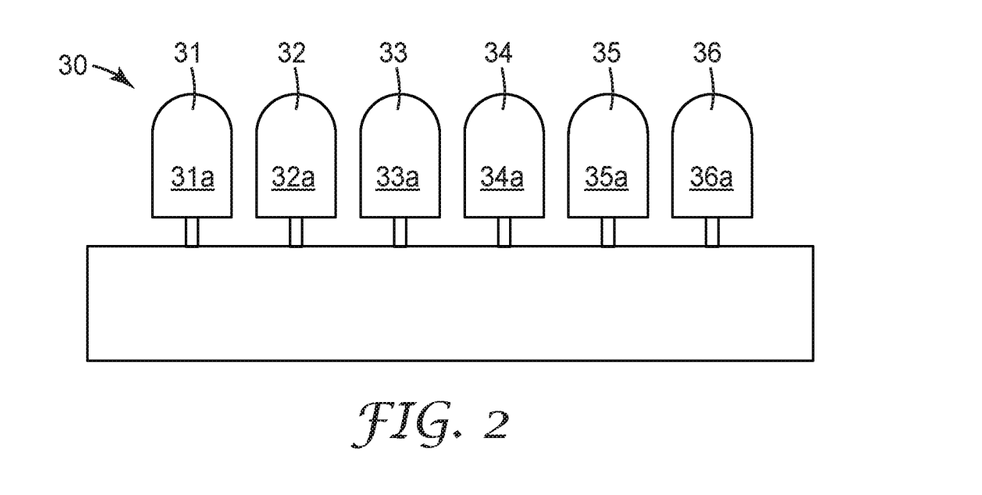
FIG. 2 is a front view on a shade guide according to an embodiment of the invention.

A target surface 20 is illustrated within the dental blank 10. The target surface 20 is virtual and corresponds to a mathematical representation of a three-dimensional surface. The target surface 20 is entirely contained within boundaries of the dental blank 10. The virtual three-dimensional target surface has a predetermined shape which correlates to a shape of a specimen surface 31a of a specimen 31 as shown in FIG. 2. The shape of the target surface 20 further approximates the shape of a tooth surface.

The example illustrates a cross-section 20' through the dental blank 10 in an area in which the virtual target surface 20 intersects with the dental blank 10. Accordingly a dental restoration cut out from the dental blank 10 in this area would essentially obtain the layer structure as defined by the target surface 20. In particular such a dental restoration would essentially obtain a color shading which comprises all four colors provided by the dental blank 10, however, only small portions of the layers 11 and 14 would be present therein, whereas the layers 12, 13 would extend entirely through the dental restoration. The skilled person will recognize that the target surface 20 is a two-dimensional structure so that a three-dimensional dental restoration would typically additionally also comprise cross-sections of a slightly different layer structure. However—as further described in detail below—the target surface may be used to provide at least an outer surface of the dental restoration with the layer structure defined by the target surface 20 or a similar layer structure.

FIG. 2 shows a shade guide 30 comprising a plurality of different shade specimens 31-36. The shade specimens 31-36 in the example have the same three-dimensional shape, but exhibit different specimen surfaces 31a-36a. In particular each of the specimen surfaces 31a-36a represents a particular color shading. For example the color shading represented by the specimen surface 31a is defined by a virtual three-dimensional target surface (shown as item 20 in FIG. 1). The target surface 20 (virtually located) within the blank 10 corresponds in shape with the shape of the specimen surface 31a. It is noted that in case the dental blank is formed of a pre-sintered porous material the target surface 20 may be proportionally enlarged with respect to the specimen surface 31a. This is because such dental blank 10 typically has an open-celled structure and a dental restoration obtained from such blank has to be proportionally oversized to account for shrinking during sintering toward a solid structure.

Figure 3:
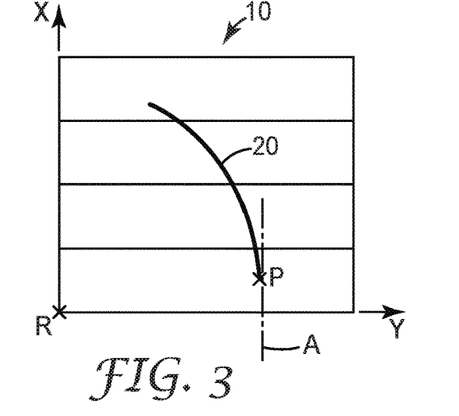
FIG. 3 is a cross-sectional view through a dental blank according to an embodiment of the invention.
Figure 4:
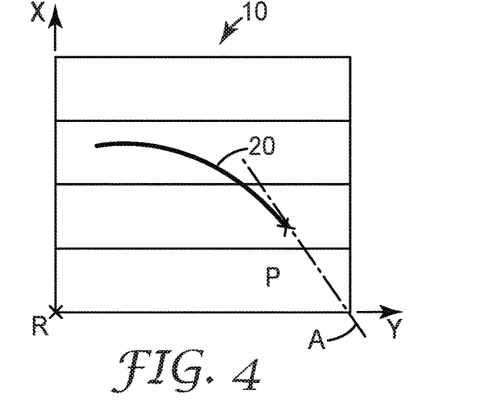
FIG. 4 is a further cross-sectional view through a dental blank according to an embodiment of the invention.

FIG. 3 and FIG. 4 are schematic illustrations of a cross-section through the blank 10 and a target surface 20 in different positions and/or orientations. As shown the target surface 20 in FIG. 3 relative to FIG. 4 defines different particular color shadings depending on the position and/or orientation of the target surface 20 within the blank. The target surface 20 has a position P relative to a blank reference coordinate R within the dental blank 20. The position of the target surface preferably relates to a pre-determined target reference coordinate P on or relative to the target surface. For example such target coordinate P may be determined at the lower right corner (see FIG. 1) of the target surface 20. The skilled person will however recognize that the target coordinate P may be pre-determined at any other appropriate location relative to the target surface 20 as long as the relation between coordinates defining the target surface 20 and the target coordinate is defined. Further the target surface 20 has an orientation relative to a reference axis X or Y within the dental blank 20. The orientation of the target surface 20 preferably relates to a pre-determined target reference axis A on the target surface 20. For example the target reference axis A may be determined as a tangent on the target surface 20 through the target coordinate P. The skilled person will however recognize that such target reference axis A may be pre-determined at any other appropriate orientation relative to the target surface 20 as long as the relation between coordinates defining the target surface 20 and the target reference axis is defined. It is noted that the orientation of the target surface is further defined by axes B and C which are arranged in a perpendicular relationship to each other and to the axis A. These two further axes are however omitted for better clarity in the two-dimensional illustration of the example.

As demonstrated by FIG. 3 and FIG. 4 different particular color shadings of the target surface can be provided by simply moving and/or orienting the target surface within the dental blank. In FIG. 3 for example the target surface 20 defines a color shading having four different colors, whereas the same target surface 20 just positioned and oriented differently defines a color shading having only two different colors. In the latter case further the two colors shown in FIG. 4 extend over larger portions of the target surface 20 than the same colors in FIG. 3. Therefore a multiplicity of equally color shaded dental blanks can nevertheless be used to provide a wide variety of differently color shaded dental restorations.

Accordingly the shade guide 30 as shown in FIG. 2 preferably has a plurality of specimen surfaces each associated with a target surface at one of a plurality of different positions and orientations. For example the specimen surface 31a in FIG. 2 may have the same shape as the reference surface 20 in FIGS. 3 and 4 and may be associated with a position and orientation of the target surface 20 as shown in FIG. 3. On the other hand the specimen surface 32a in FIG. 2 may be associated with the same target surface 20 but at a different position and orientation within the dental blank.

Figure 5:
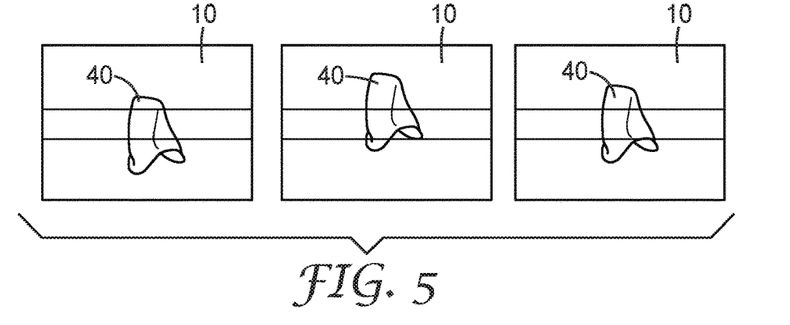
FIG. 5 illustrates a dental restoration at different positions within a dental blank according to an embodiment of the invention.

FIG. 5 shows a (virtual) dental restoration at the same orientation but at different positions within the blank. As shown the color shading of the dental restoration depends on the position of the dental restoration. To determine the position of a dental restoration within the blank in a first step the shade guide may be used to determine a particular color shading. Because the specimens of the shade guide are associated with a target surface at a particular position within the dental blank the associated target surface can in a further step be used to define the position of a surface of the dental restoration and thus of the dental restoration itself. The surface used for positioning the dental restoration preferably corresponds to an outer visible surface of the final dental restoration, particularly such surface which is intended to obtain the color shading initially determined by the shade guide.

Figure 6:
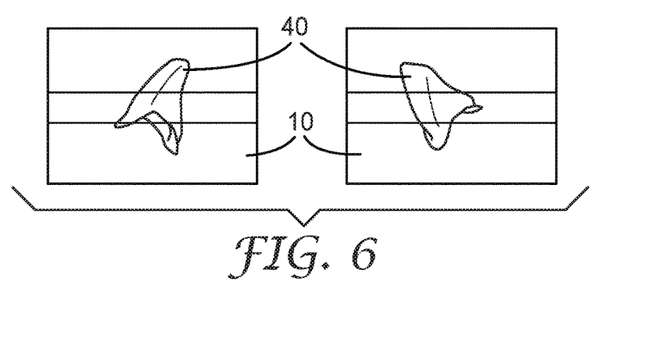
FIG. 6 illustrates a dental restoration at different inclinations within a dental blank according to an embodiment of the invention.
Figure 7:
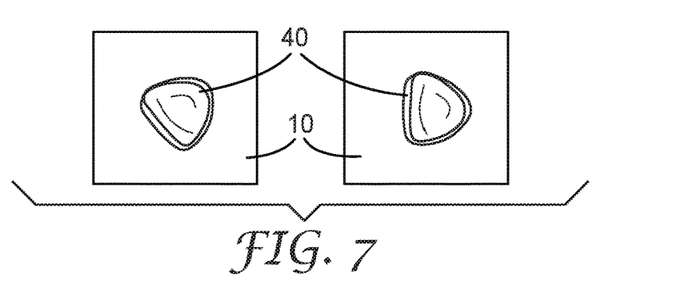
FIG. 7 illustrates a dental restoration at different rotations within a dental blank according to an embodiment of the invention.

FIGS. 6 and 7 illustrate that the dental restoration may further have different inclination angles (FIG. 6) and/or different rotation angles (FIG. 7). FIG. 6 shows different inclinations in only one dimension, however, the skilled person will recognize that further inclinations are possible in a further dimension (perpendicular to the plane of the Figures). Thus the invention allows the making of a variety of differently color shaded dental restorations by machining the dental restorations at different positions and or orientations from equally color shaded dental blanks.

The skilled person will recognize the instead or in addition to a color shading the blank may have a transparency gradient. Accordingly what is described for the color shading identically applies for any transparency gradient of the dental blank and/or the dental restoration.

In the following the method of making the dental restoration is explained in further detail.

Figure 8:
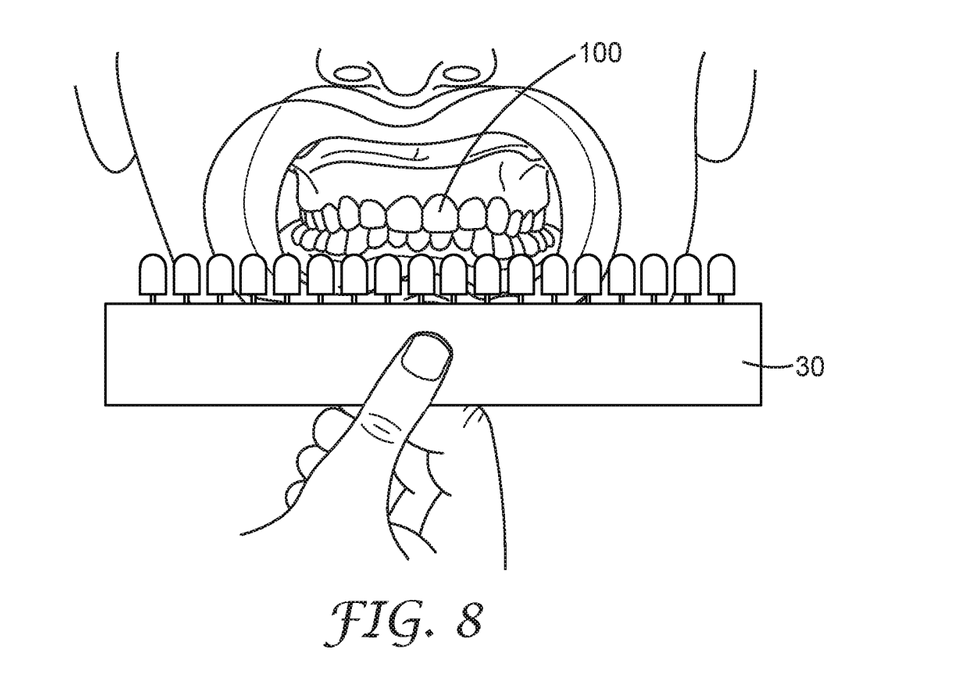
FIG. 8 illustrates the matching of a color shading using a physical shade guide according to an embodiment of the invention.

FIG. 8 illustrates the visual matching of a shade specimen of the shade guide 30 with a tooth 100 of a patient. In the example a user, for example a dentist, uses a physical shade guide and positions a shade specimen it next to a patient's tooth 100 to be restored. The user typically compares the color shading of different shade specimens with the actual color shading of the patient's tooth and selects the shade specimen which matches best. The skilled person is aware that the same matching step can be performed with one of the neighboring teeth of the patient's tooth to be restored, for example in case the tooth to be restored is missing or otherwise unsuitable or unavailable for color matching.

Each shade specimen of the shade guide 30 is associated with a predetermined position and orientation of a (virtual) target surface in a (virtual) dental blank. Accordingly the shade guide may have a code for each shade specimen that represents or allows obtaining the associated predetermined position and orientation within the dental blank. Further the shade guide and/or the shade specimens may be associated with a certain type of color shaded dental blank, so that for differently color shaded blanks further shade guides and/or shade specimens may be available. Therefore the code may further comprise information about the type of dental blank which the shade guide and shade specimen is associated with.

Figure 9:
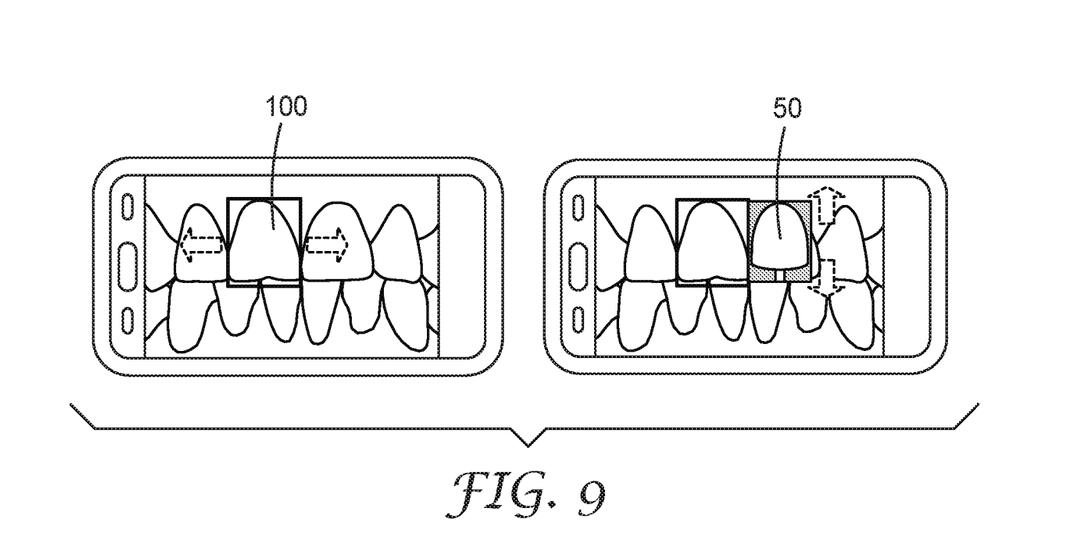
FIG. 9 illustrates the matching of a color shading using a virtual shade guide according to an embodiment of the invention.

FIG. 9 shows the matching of a virtual shade specimen 50 with a tooth 100 of a patient. In the example a user, for example a dentist, uses an image of the patient's teeth in combination with a computer simulated or virtual shade guide. The image may be taken real time, for example via a live camera, or in advance of the matching, for example by a photo camera. Such image is preferably visualized to the user on a screen of a computer. The computer may have implemented a virtual shade guide comprising a plurality of differently color shaded shade specimens. Further the computer may provide for a switching option allowing a user to switch between different shade specimens. In the example a shade specimen 50 is displayed besides the tooth to be restored 100 in an overly of the shade specimen 50 on the image. The user may accept the specimen 50 by a user input or switch to and accept another specimen stored in the computer, and thereby perform the matching. The computer may further have functionality to measure the degree of the matching between the tooth and a certain specimen, for example by a statistical comparison of the color distribution on the tooth relative to the shade specimen. Further the computer may have functionality to propose a certain shade specimen based on a color measurement of the patient's tooth or the image of the patient's tooth.

In this example the computer preferably has stored information about the shade specimens and the associated position and orientation of the target surface within the blank. Preferably position and orientation of the target surface within the blank is automatically determined upon selection of a shade specimen.

Figure 10:
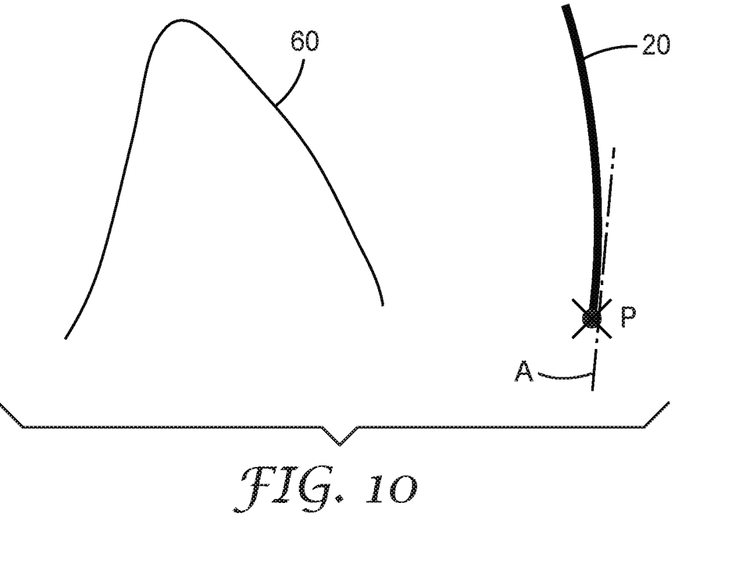
FIG. 10 illustrates the design of a dental restoration based on the target surface according to the invention.
Figure 11:
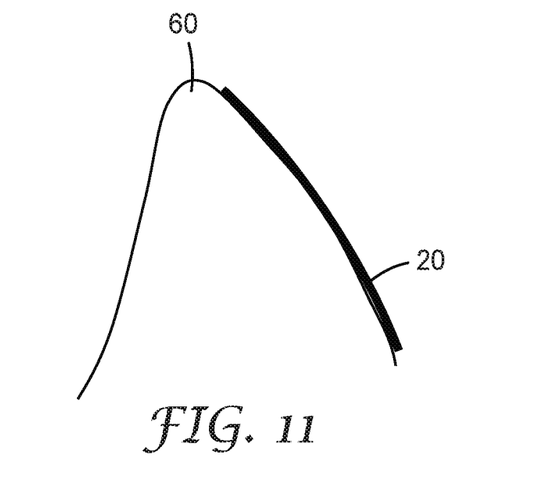
FIG. 11 illustrates the design of FIG. 10 at a different design stage.

FIG. 10 and FIG. 11 illustrate—for better clarity in a two-dimensional view only—one way of using the target surface according to the invention to create a dental restoration. In particular a target surface 20 is provided virtually, for example in the form of a three-dimensional computer representation within a (dental) CAD system. The target surface 20 has a standardized shape approximating an outer tooth surface (for example a labial surface of a human average incisal tooth). Further a three-dimensional computer representation of the dental restoration is provided within the CAD system. Such a virtual dental restoration may be obtained from designing by a user. For designing a dental restoration, typically at least part of a patient's dentition is captured (for example scanned) and the captured data is provided to the CAD system in the form of a three-dimensional computer representation. Based on this the user may design a restoration of a tooth to be restored. The CAD system may have a database from which certain standard tooth shapes may be retrieved, and a user may adapt such a standard tooth shape in accordance to the geometric situation of the patient's dentition. Or the user may design the entire restoration by use of CAD software tools, accounting for the geometric limitations present in the patient's dentition.

The CAD system preferably allows a user to three-dimensionally move and rotate the target surface 20 and the dental restoration relative to each other. Accordingly the user may manually combine the target surface 20 and a surface of the dental restoration 60 as illustrated in FIG. 11. However the CAD system may further have functionality to determine an average orientation of the surface of the dental restoration 60 and adapt the orientation of the target surface 20 accordingly. Further the CAD system may further have functionality to automatically combine the target surface 20 and the surface of the dental restoration 60 so that the target surface 20 and the surface of the dental restoration 60 intersect.

The target surface 20 being selected by the shade guide of the invention is preferably associated with a shade specimen of the shade guide and thus with a position and orientation within a color shaded dental blank. Accordingly such position and orientation associated with the specimen may be used to determine a correlating position and orientation within the blank. Because target surface 20 is combined with the virtual dental restoration 60 (and thus the target surface 20 and the virtual dental restoration 60 are in a determined geometric relationship) the dental restoration can be machined out of the blank at a position and orientation as associated with the target surface 20. Thereby the position and orientation is preferably a relative position and orientation from a reference position and reference orientation of the blank.

The position and orientation associated with the target surface is preferably transmitted to a device for machining the dental blank, for example a milling machine. The dental restoration, or a precursor thereof, can then be machined from the dental blank at the correlating position and/or orientation. It is noted that in case a pre-sintered dental blank is used the position and orientation associated with the target surface may include an offset at least in dimensions defining the position. This is to account for any shrinkage resulting from sintering the blank or restoration precursor toward the final density.

What is claimed is:

1. A system comprising at least one dental blank and an associated physical shade guide, the dental blank exhibiting a non-uniform color shading in at least one dimension, and the physical shade guide comprising a plurality of physical shade specimens each exhibiting a specimen surface, wherein each specimen surface has a three-dimensional shape and further exhibits a particular non-uniform color shading defined by a virtual three-dimensional target surface of a correlating shape and non-uniform color shading within the dental blank, wherein each of the plurality of physical shade specimens is associated with a respective virtual three-dimensional target surface having a predetermined position and orientation in the dental blank, wherein each of the respective virtual three-dimensional target surfaces has at least one of different positions and different orientations in the dental blank, and wherein each of the respective virtual three-dimensional target surfaces has a shape corresponding to the respective specimen surface.

2. The system of claim 1, wherein the dental blank is made of differently colored materials which in combination provide the dental blank with the non-uniform color shading.

3. The system of claim 1, wherein a three-dimensional shape of the specimen surface is non-planar.

4. The system of claim 1, wherein the dental blank further exhibits a non- uniform transparency gradient in at least one dimension, and wherein each physical shade specimen represents a particular transparency gradient present in the dental blank or obtainable from the dental blank adjacent the target surface within the dental blank.

5. The system of claim 1, wherein the position is defined by three coordinates in a three-dimensional Cartesian coordinate system, and wherein the orientation is defined by a first inclination angle about a first axis, a second inclination angle about a second axis and a rotation angle about a third axis of the same Cartesian coordinate system.

6. The system of claim 1, wherein each specimen surface is assigned a code representing information about the non-uniform color shading and information about the position and orientation of the target surface in the dental blank.

7. The system of claim 1, wherein the dental blank is formed of a pre-sintered ceramic material having an open porous structure, and wherein each of the respective virtual three-dimensional target surfaces corresponds to a proportionally enlarged shape of the specimen surface.

8. The system of claim 1, wherein the dental blank is formed of a solid block of material, and wherein each of the respective virtual three-dimensional target surfaces is equal to the three-dimensional shape of the respective specimen surface.

9. The system of claim 8, wherein the dental blank is formed of a dental composite, a dental ceramic, or a dental glass ceramic.

10. A system comprising at least one dental blank and an associated physical shade guide, the dental blank exhibiting a non-uniform color shading in at least one dimension, and the physical shade guide comprising a plurality of physical shade specimens each exhibiting a specimen surface, wherein each specimen surface has a three-dimensional shape and further exhibits a particular non-uniform color shading defined by a virtual three-dimensional target surface of a correlating shape and non-uniform color shading within the dental blank, wherein each of the plurality of physical shade specimens is associated with a respective virtual three-dimensional target surface having a predetermined position and orientation in the dental blank, wherein each of the respective virtual three-dimensional target surfaces has at least one of different positions and different orientations in the dental blank, and wherein each of the respective virtual three-dimensional target surfaces has a shape (i) equal to the three-dimensional shape of the corresponding specimen surface, or (ii) that is a proportionally enlarged shape of the three-dimensional shape of the corresponding specimen surface.

\* \* \* \* \*